(12) United States Patent
Fleischli et al.

(10) Patent No.: US 8,631,680 B2
(45) Date of Patent: Jan. 21, 2014

(54) METHOD FOR THE CALIBRATION OF A FLOW MEASUREMENT IN A FLOW SYSTEM, AND FLOW SYSTEM FOR CARRYING OUT THE METHOD

(75) Inventors: Andreas Fleischli, Baar (CH); Thomas Gempp, Rudolfstetten (CH)

(73) Assignee: Thoratec LLC, Pleasanton, CA (US)

( * ) Notice: Subject to any disclaimer, the term of this patent is extended or adjusted under 35 U.S.C. 154(b) by 916 days.

(21) Appl. No.: 12/217,269

(22) Filed: Jul. 1, 2008

(65) Prior Publication Data

US 2009/0064755 A1 Mar. 12, 2009

(30) Foreign Application Priority Data

Sep. 11, 2007 (EP) .................................... 07116095

(51) Int. Cl.
*G01F 25/00* (2006.01)

(52) U.S. Cl.
USPC .......................................................... 73/1.16

(58) Field of Classification Search
None
See application file for complete search history.

(56) References Cited

U.S. PATENT DOCUMENTS

| | | | |
|---|---|---|---|
| 4,831,866 A * | 5/1989 | Forkert et al. ................... 73/1.27 |
| 4,923,598 A * | 5/1990 | Schal ............................... 210/87 |
| 5,318,409 A * | 6/1994 | London et al. .................. 417/53 |
| 6,278,251 B1 * | 8/2001 | Schob ............................ 318/293 |
| 6,629,447 B1 * | 10/2003 | Collins .......................... 73/1.16 |
| 2004/0039243 A1 | 2/2004 | Bearnson et al. |
| 2007/0073393 A1 | 3/2007 | Kung et al. |

FOREIGN PATENT DOCUMENTS

WO WO 02/45775 A2 6/2002

* cited by examiner

*Primary Examiner* — Robert R Raevis
(74) *Attorney, Agent, or Firm* — Kilpatrick Townsend & Stockton LLP

(57) ABSTRACT

A flow rate of a fluid in a flow system is determined based on one or more parameters of the flow system, the parameters not including the flow rate itself. The flow rate is also measured with a calibration sensor, and the measured flow rate is used to calibrate how the flow rate is determined.

18 Claims, 8 Drawing Sheets

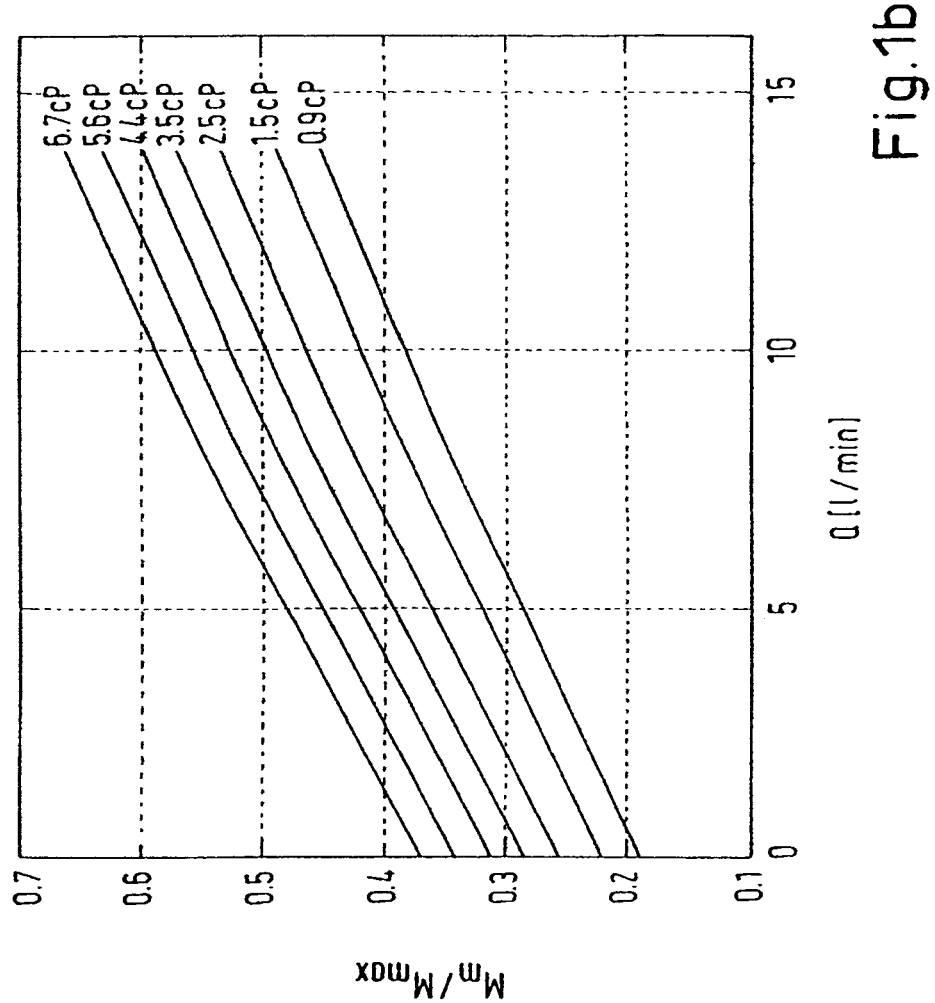

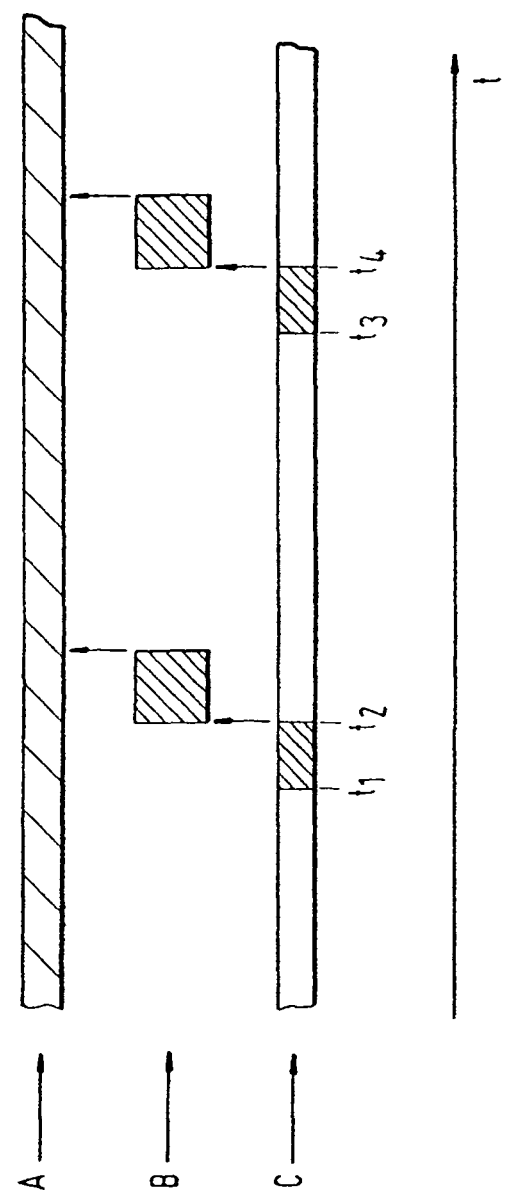

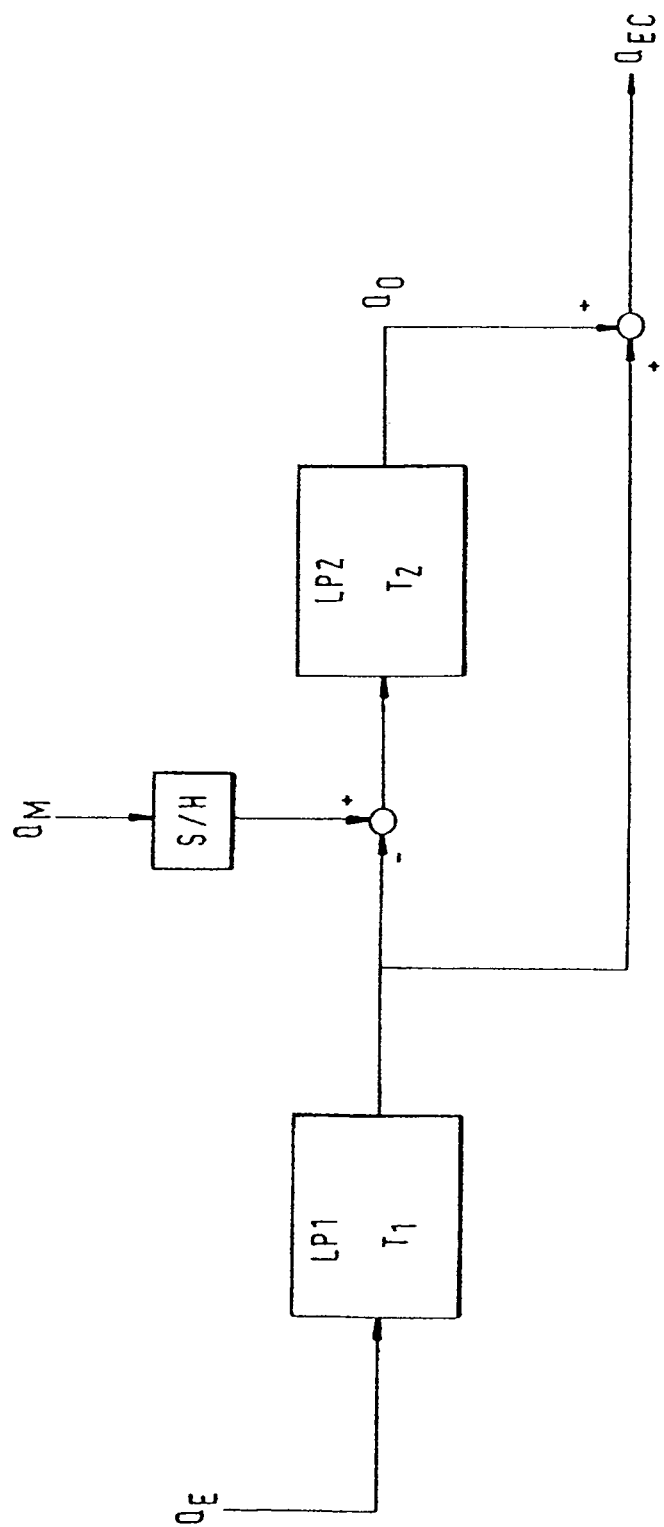

METHOD FOR THE CALIBRATION OF A FLOW MEASUREMENT IN A FLOW SYSTEM, AND FLOW SYSTEM FOR CARRYING OUT THE METHOD

CROSS-REFERENCE TO RELATED APPLICATIONS

This application claims the priority of European Application No. 07116095.6, filed on Sep. 11, 2007, the disclosure of which is incorporated herein by reference.

BACKGROUND OF THE INVENTION

The invention relates to a method for the calibration of a flow measurement in a flow system, and also to a flow system for carrying out the method.

It is barely possible to keep pace with the number of methods and applications which are now known for the measurement of flow, in other words for the determination of the amount of a fluid that is pumped through a flow system per unit of time.

Flow rates are measured for liquids, for example in injection systems for combustion engines, such as for motor vehicles, airplanes, or ships. Flow rates of crude oil through pipelines have to be measured and monitored continuously, for example for invoicing purposes. In the filling of containers, filling quantities have to be measured and metered, etc.

It is nowadays standard practice to make flow measurements of gaseous fluids, such as natural gas through a pipeline, or for invoicing purposes when refueling motor vehicles, with the aid of the most varied systems.

In this connection a large number of physical values and characteristics of the fluid or of the flow system are available for the determination of the amount flowing, through the measurement of which the amount of the fluid flowing through the flow system can be determined.

The parameter which is specifically used for the measurement of the amount flowing in any given case can depend on many factors. It can depend, on the one hand, on whether the fluid is liquid or gaseous, or even solid, such as for example fine abrasive sand flowing in a sandblasting device or a fine spray powder flowing in a thermal spraying apparatus. As used herein, the term "fluid" should be understood to include granular and powdered solids. Certain parameters are then suitable or not suitable from the outset. Thus, for example, in the determination of the flow of a gas, special efforts have to be made since, for example, the measurement of the volume flowing per unit of time through the flow system only makes limited statements about the amount of mass flowing, since with a given volume flow this depends very much on the temperature and the pressure of the gas, for example.

In the flowing transport of liquid materials, on the other hand, values such as the pressure and the temperature of the fluid often do not play a role, so that—at least when no real precision is demanded—a measurement of the volume flowing through the flow system per unit of time is completely adequate to draw conclusions on the mass of material which has actually flowed.

Thus, it is often possible and also appropriate to provide within a flow connection of the flow system simple sensors, such as impellers, floating bodies, aperture diaphragms for measuring in accordance with the differential pressure method, venturi nozzles (in the case of gases), and many other measuring devices well-known to the person averagely skilled in the art, so that the flowing fluid can interact directly with the corresponding measuring device (with the impeller for example), so that the flow rate is directly deducible, for example from the rotary speed of the impeller.

Thus, in simple cases, i.e. when no really strict demands are made on the precision of the flow measurement and/or when, for example, no hygienic or technically sensitive liquids have to be measured, such as blood, pharmaceutically or chemically ultra-pure liquids, or ultra-pure liquids in the semiconductor industry, for example slurries for the polishing of semiconductor wafers, a plurality of measuring systems and methods are available which are partly interchangeable at will and which completely fulfil the technical requirements in relation to precision, long-term stability and chemical or physical compatibility with the fluid to be measured.

Greater efforts have to be made, however, when the demands on the flow measurement increase. For example, during the measurement of liquids, temperature fluctuations or alterations in pressure can influence the measurement result, when precision of the results is required. Depending on the method of measurement, other parameters, such as the viscosity of the fluid for example, which can change in the course of the measuring process, can unacceptably influence the results.

It is also of the greatest significance in some applications that the measurement does not take place invasively, if at all possible. I.e. it is often essential that the measuring device as such does not come into direct physical contact with the fluid to be measured. This can be significant, for example, when the fluid is not compatible with the measuring body, for example chemically or physically, for example because the fluid is very aggressive chemically as in the case of a strong acid or lye, or is physically aggressive, such as for example the above-mentioned slurry, which acts highly abrasively and could destroy a measuring body, such as a floating body or an impeller, in a very short time.

However, not only can the measuring apparatus be affected negatively by the fluid to be measured; vice versa, in some cases the measuring apparatus can also have negative repercussions on the fluid to be measured.

Thus, in the case of sensitive liquids, such as blood or ultra-pure pharmaceutical or chemical products, impurities have to be avoided at all costs. In the case of a mechanical bearing for example, in which an impeller is journalled for the measurement of the flow rate, this can lead to contamination of the fluid in the flow system in the form of bearing lubricants or mechanically abraded particles.

For example, blood is a liquid which also reacts to mechanical influences extremely sensitively. If the flow system is a ventricle support system for the support of a human or animal blood circulation, in other words a flow system made of a blood pump, cannulae and feed lines, which forms a bypass for the heart during an operation for example, or supports a weakened heart in a long-term application, the quantity of blood flowing is a very critical system parameter, which has to be monitored constantly and possibly sensitively readjusted by suitably controlling the blood pump.

In a flow system of this kind the measurement of the flow rate of the blood is a particularly critical challenge with regard to various aspects.

If constrictions and/or a locally heavy mechanical load arises in the ventricle support system, for example a compression of the blood between an impeller of a flow measuring component and a wall of the flow connection, then a destruction or crushing of the red blood corpuscles can result, or adsorption and/or accretion of blood on the flow measuring body, for example on an impeller for flow measurement, can take place and, in the worst case, can even lead to severe agglutination of the blood, which can lead to serious damage to the patient, such as thromboses, vascular occlusions and even to infarct, in the worst case to the death of the patient.

For this reason in medical systems such as these—however, also in purely technical systems, for example for the semi-conductor industry where, as described above, very high purity is required—additional invasive measuring apparatuses are preferably not provided in the flow system in order to monitor the flow rates of the fluid to be pumped.

SUMMARY OF THE INVENTION

It is an object of the present invention to make available a method for the calibration of a flow rate in a flow system, in particular in a portable ventricle support system, and also a flow system, especially a ventricle support system, with which the flow rate of the fluid can be determined by the flow system reliably and for long periods of up to days, weeks or months, typically up to six months or longer, and can in particular be determined non-invasively, with the consumption of electrical energy for the carrying out of the flow measurement being minimized at the same time.

As mentioned above, invasive measuring apparatuses are preferably not provided in the flow system in order to monitor the flow rates of the fluid to be pumped. One attempts, rather, to derive the flow rates from operating data of the system which are available anyway. If a system such as this contains a pump—for example, in a ventricle support system for the support or short-term replacement of the function of a patient's heart—then the flow rates can for example be deduced by evaluating the operating data of the electrical pump motor.

To this end, electrical operating data of the motor—for example the take-up of electrical power by the pump motor, especially the electrical current drawn by the pump motor, in particular the drive current; and the speed of rotation of the rotor—are significant input parameters for the calculation of the flow in an embodiment which is particularly relevant for practical use. They have to be constantly monitored and recorded and from them the flow rates can be determined, for example with the assistance of a look-up table or other calculation methods.

This method has proved valuable above all in the use of so-called bearingless motors, as will be described in more detail later, because in this type of motor the flow rates can be deduced very simply and reliably from the electrical operating data of the motor. Then no additional technical elements are necessary for the measurement of the flow, which interact invasively with the circulating blood or, in the case of non-medical flow systems, with other fluids.

BRIEF DESCRIPTION OF THE DRAWINGS

The invention will be described in more detail in the following with the help of the drawings.

FIG. 1b illustrates the relationship between torque and flow rate of liquid blood substitutes of different viscosities at a constant speed of rotation;

FIG. 2a schematically illustrates a calibration method;

FIG. 2b schematically illustrates a diagram of a calibration algorithm;

DESCRIPTION OF THE PREFERRED EMBODIMENTS

One possible concept for the determination of the flow from the corresponding power curves of the pump or of the pump drive will be explained in the following.

Figure 1A:
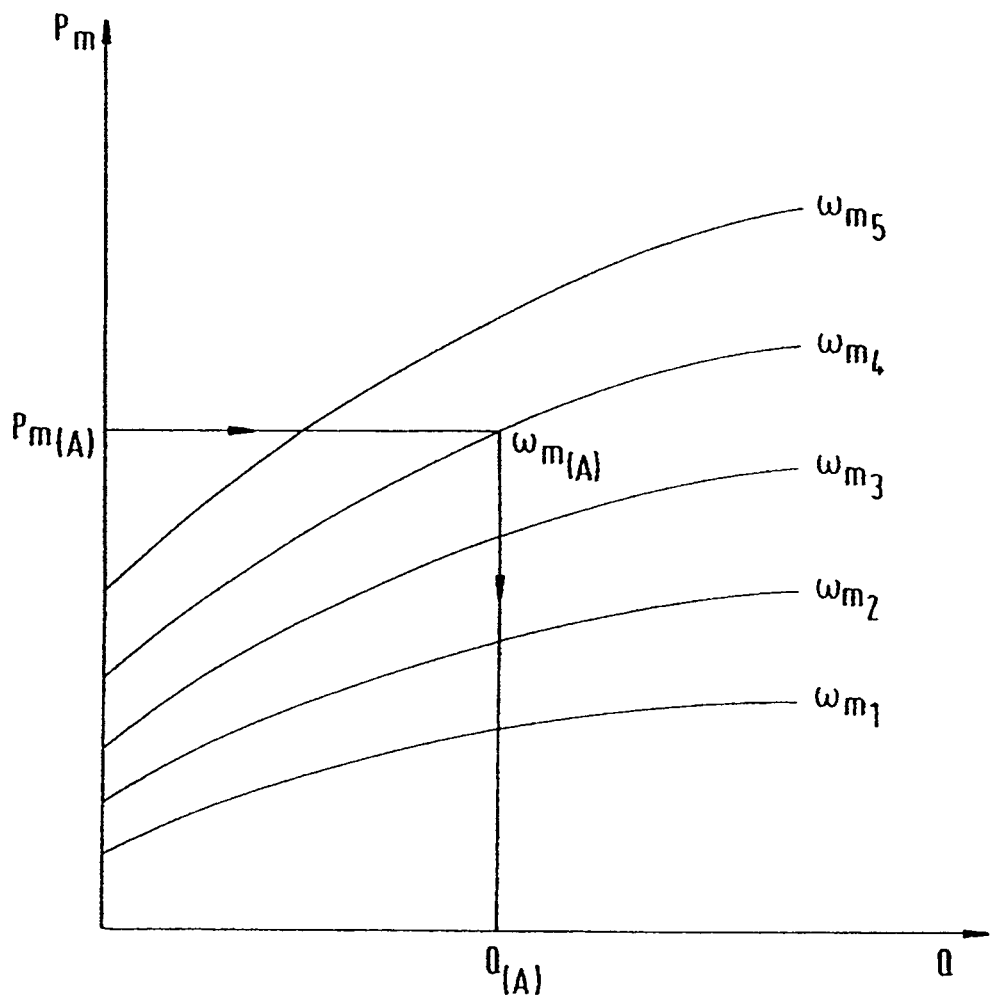
FIG. 1a illustrates the relationship between mechanical power and flow rate at various angular speeds.

The symbols used, such as are also to be found in part in FIGS. 1a and 1b, normally have in this connection the following meaning: $P_m$ is the mechanical power delivered at the rotor; M is the total motor torque; $M_m$ is the mechanical torque delivered at the rotor; $M_L$ is the hydraulic load torque; $M_I$ is the idling torque; $\omega_m$ is the mechanical angular frequency, which is directly proportional to the rotational speed of the rotor; Q is the flow rate flowing through the pump; $I_M$ is the torque current; $\gamma_m$ is the mechanical rotor angle; and $c_M$ is a torque constant.

The power curves give the relation between mechanical power $P_m$ and hydraulic output, which determine the flow rate Q in a pump. They are, as schematically illustrated in FIG. 1a, a set of curves wherein the parameterization takes place with the speed of rotation $\omega$ of the rotor. Each individual curve represents the relation between the mechanical power $P_m$ and the flow rate through the pump at a constant speed of rotation $\omega_m$. The mechanical power can be calculated after the determination of the torque $M_m$ and the speed of rotation $\omega_m$:

$$Pm = M_m \cdot \omega_m$$

If the pump characteristics are known, the flow rate through the pump can be ascertained from the power curves, taking account of the calculated mechanical power and the speed of rotation of the rotor.

With a constant speed of rotation, the torque $M_m$ is directly proportional to the mechanical output $P_m$. Due to the friction-free magnetic bearing, the magnetic moment $M_m$ corresponds directly to the hydraulic load torque $M_L$.

In the case of an UltraMag system, which the assignee markets, one achieves an adequate degree of precision with interpolation of the power curves which is linear with respect to the flow.

$$M_m = M_L = c^{(P1)}(\omega_m) \cdot Q + c^{(P0)}(\omega_m)$$

The coefficients $c^{(P0)}$ and $c^{(P1)}$ are dependent on the speed of rotation of the rotor:

$$c^{(P0)}(\omega_m) = c_2^{(P0)} \cdot \omega_m^2 + c_1^{(P0)} \cdot \omega_m$$

$$c^{(P1)}(\omega_m) = c_1^{(P1)} \cdot \omega_m$$

From this:

$$M_m = M_L = (c^{(P1)} \cdot (\omega_m) \cdot Q + c_2^{(P0)} \cdot (\omega_m)^2 + c_1^{(P0)} \cdot (\omega_m)$$

From this, flow rate Q results:

$$Q = (M_m - (c_2^{(P0)} \cdot \omega_m^2 + c_1^{(P0)} \cdot \omega_m^2)) / (c_1^{(P1)} \cdot (\omega_m))$$

The torque calculation and the calculation of the speed of rotation will also be discussed in somewhat more detail in the following.

The torque M is needed for the calculation of the flow rate and is calculated from the torque constant $c_m$ of the motor and the torque forming torque current $I_M$ of the motor.

$$M = c_M \cdot I_M$$

This torque M is composed of the idling torque $M_1$ which takes care of the internal losses of the motor and the mechanical torque $M_m$ transmitted at the rotor. From this there results $$M = M_1 + M_m$$

Both the torque constant $c_m$ and also the idling torque $M_1$ are dependent on the speed of rotation. From this results:

$$M_m = c_M(\omega_m) \cdot I_M - M_1(\omega_m)$$

The torque current is measured and is known in the system.

For the calculation of the speed of rotation the rotor angle $\gamma_m$ is determined via a field measurement with all probes. The derivative of the rotor angle $\gamma_m$ results in the speed of rotation $\omega_m$:

$$\omega_m = d\gamma_m / dt$$

As an alternative method the speed of rotation $\omega_m$ can also be determined from the induced voltage of the drive phases, which does not have to be implemented however.

All of the variables mentioned in the above passage can be deemed parameters of the pump, or more generally, of the flow system. Namely, the parameters mentioned above include torque of the pump, electrical drive current of the pump, power of the pump, angular velocity of the pump, angular frequency of the pump, and induced voltage of drive phases of the pump. Other parameters can additionally or alternatively be used, and should be understood to be within the scope of the appended claims.

The pumped medium also has a decisive influence in this connection, in other words for example the pumped medium blood. The power curve of the blood pump is namely also dependent on the density and the viscosity of the blood.

In practice the density of the blood only alters slightly and in many cases may be regarded as constant to a first approximation.

In contrast, the blood viscosity varies considerably and is, as known per se to the person averagely skilled in the art, dependent on different parameters, such as hematocrit, male/female, smoker/non-smoker, temperature, cholesterol level, body fitness index, etc.

In normal cases the hematocrit value is in the region of 35-50%. If extreme cases are taken into consideration, a hematocrit range between 15 and 60% is to be expected. According to "Jürgen Hahn, sensor-less determination of the process factors of magnetic bearing blood pumps, dissertation ETH Zurich, No. 14563, Zurich 2002", the content of which is hereby incorporated by reference into this application, the following connection between hematocrit and the viscosity will be shown in Table 1:

TABLE 1 the relation between haematocrit and viscosity

| HCT In % | Dynamic viscosity in cylindrical portion | | |
|---|---|---|---|
| 15 | 2.05 | | |
| 35 | 2.89 | | |
| 40 | 3.26 | normal range | widened range |
| 45 | 3.74 | | |
| 50 | 4.36 | | |
| 60 | 6.1 | | |

This shows that the viscosity varies considerably, simply due to the varying hematocrit.

Theory and practice show that the dynamic viscosity coefficients $c_2^{(P0)}$ and $c_1^{(P0)}$ of the power curves in the equation $$M_m = M_L = (c_1^{(P1)} \cdot \omega_m) \cdot Q + c_2^{(P0)} \cdot \omega_m^2 + c_1^{(P0)} \cdot \omega_m$$

are dependent on the viscosity of the pumped liquid.

In addition, FIG. 1b shows the power curves with liquid blood substitutes of differing viscosities at a constant speed of rotation. The ratio of the maximum mechanical torque $M_{max}$ to the mechanical torque $M_m$ given off at the rotor is plotted against the flow rate Q in liters per minute. The power requirement rises with increased viscosity and the power curves shift upwardly in parallel. This means that essentially only the offset value of the curves is influenced by the viscosity.

By the use of this special technique known per se the flow of the fluid can thus be determined by a flow system, without resulting in negative effects or influences on the fluid.

It has been shown, however, that even with these systems, at least then when the highest demands are made on the precision of the flow rate measurement or on the operating safety of the system as a whole, there is still considerable room for improvement.

Thus, for example, the flow rate of the fluid determined from the electrical operating data depends within certain limits on the viscosity and/or the temperature and/or the gas loading and/or on other physical or chemical conditions of the fluid. For example, in the case of blood, the viscosity can vary due to different factors, such as, for example, the composition of the blood, the loading with gases, the temperature, etc. within limits which are completely relevant for the flow measurement.

This can lead to the fact that the flow rates determined from the electrical operating data show deviations from the actual flow rate over time. These could be periodically fluctuating or non-periodically fluctuating deviations or also drifting movements developing over a long period, so that after a certain length of operating time the flow rates determined from the pumping data deviate from the actual flow rate amounts more and more.

It is clear that due to such erroneous flow rate data a reliable regulation and/or control and/or evaluation of the flow system—above all such a sensitive system as a ventricle support system—is no longer possible and can even possibly have fatal consequences for a patient connected to that system.

It is thus evident that additional measures will have to be taken for the securing of a reliable measurement of the flow rates.

The possibility of determining the flow rate by means of an internal, if at all possible non-invasive, measuring apparatus which essentially reacts insensitively to the above-described fluctuations in the system, such as fluctuations of temperature, viscosity, etc., is evident and thus supplies reliable measurement data regarding the flow rate of the fluid.

A method with which this is in principle possible consists of the measurement of the transit time of a short ultrasonic impulse, or of packets of ultrasonic waves, which, for example, is or are sent by a first transmitter against the flow direction of the fluid through the flowing fluid and are received by an acoustic second receiver axially displaced against the flow direction. In modern devices the transit time difference is determined using so-called DSPs in a manner known per se, wherein cross-correlation methods are often used.

In this connection the aforementioned second receiver can be operated in turn as a second transmitter, which likewise sends a short ultrasonic impulse or the packet of ultrasonic waves through the fluid—this time in the flow direction of the fluid—to the first transmitter, which can be simultaneously operated as a second receiver for the reception of the ultrasonic impulse or of the packet of ultrasonic waves from the second transmitter.

The transit time of the ultrasonic impulse or packet of ultrasonic waves measured against the flow direction of the fluid is compared with that transit time of the ultrasonic impulse or with that transit time of the packet of ultrasonic waves that has or have passed through the flowing fluid in the flow direction. Then the flow speed of the fluid can be determined from the transit time difference of the two ultrasonic impulses or the packets of ultrasonic waves in a manner well-known to the person averagely skilled in the art.

In cases in which the flow speed and/or the density of the fluid does not depend in a relevant manner or significantly on the possible fluctuations of the system parameters, i.e. on the possible fluctuations of the temperature, the viscosity, etc., the flow rate can be reliably determined directly from the determined flow speed of the fluid with known geometry of the flow system or of a flow connection at which the measurement is taken, without the aforementioned fluctuations negatively influencing the measurement result.

It is clear that not only acoustic systems can be used as an additional measuring system. In principle, mechanical, inductive, capacitive or optical measuring systems are also suitable, with which the flow rate is suitably and reliably determinable via a suitable parameter of movement of the fluid, via its flow speed for example.

However, above all then, when the electrical energy necessary for the operation of the system is not available to a sufficient extent or is difficult to make available, corresponding disadvantages have to be accepted in relation to the energy supply of the flow system.

Above all, the additional electronics which are needed to operate and evaluate the additional measurement system can consume a considerable amount of additional electrical energy, which is not tolerable or at least can only be compensated for with difficulty.

A prominent example of a flow system such as this are ventricle support systems for the support of blood circulation which have already been mentioned several times, especially for the support or temporary replacement of the heart activity of a patient.

An embodiment which is particularly important in this connection are portable systems which give a patient the maximum possible freedom of movement, so that he is no longer constantly confined to bed but can move more or less freely. This is particularly important in those cases where the patient has to permanently carry the ventricle support system for a long time, for example for several days, weeks or even months, for example because his heart has to be relieved for a long time due to the bypass made available by the ventricle support system, in the hope that the diseased heart will be thus regenerated or repaired permanently or, however, for example until the pre-requisites for a heart transplantation have been established.

In portable ventricle support systems such as these, the patient has to carry around a corresponding electrical energy supply, for example in the form of batteries or accumulators, since both the blood pump of the system, and also the total associated control and evaluation electronics, have to be permanently supplied with electrical energy.

It goes without saying that in a system such as this, the level of the energy consumption is an extremely critical value which is to be minimized at all costs.

Thus, the additional apparatus, including electronics for the determination of the flow data of the fluid, has a negative effect in relation to the consumption of electrical energy so that too often the electrical energy store, which is carried about, has to be charged again or has to be exchanged, a complexity which is to be minimized as much as possible for obvious reasons. Furthermore, additional heat is produced by the additional power consumption, which is not desirable in many cases or even harmful.

It is therefore an object of the present invention to make available a method for the calibration of a flow rate in a flow system, in particular in a portable ventricle support system, and also a flow system, especially a ventricle support system, with which the flow rate of the fluid can be determined by the flow system reliably and for long periods of up to days, weeks or months, typically up to six months or longer, and can in particular be determined non-invasively, with the consumption of electrical energy for the carrying out of the flow measurement being minimized at the same time.

Thus, in accordance with the invention, a method for the calibration of a flow rate determination in a flow system is proposed, wherein a fluid is conveyed through a flow connection of the flow system, and a flow rate of the fluid is determined from a working parameter of the flow system without actually being measured. In accordance with the invention the flow rate thus determined is calibrated with a calibration sensor at a pre-determined point in time.

It is important for the invention that the actual flow rate is determined by the evaluation of one or more working parameters of the flow system, in other words, for example, from the energizing current and/or from the speed of rotation of a pump of the system. Thus, the actual flow determination does not require any additional energy and no additional apparatuses, which have to be supplied for the operation with electrical energy constantly for the determination of the flow of the fluid through the flow system.

It was in fact recognized for the first time through the invention that a more or less regular correction of the flow data determined from the working parameters suffices completely to compensate even long-term fluctuations or deviations due to changes in the flow system, for example due to changes in the viscosity of the fluid, due to temperature fluctuations or due to other changes in the system, so that long-term reliable data of the flow rate for the control and/or regulation of the flow system are also available.

By means of the method in accordance with the embodiments of the present invention a short-term calibration measurement of the flow rate of the fluid is thus only necessary from time to time. No measurements with the calibration sensor are necessary between the individual short-term calibration measurements, and all the electronics for the operation and evaluation of the calibration sensor are preferably switched off between two calibration measurements or put into a condition in which the power consumption is reduced drastically. As a result, a significant amount of electrical energy can be saved, which in a particular embodiment of a flow system in accordance with the invention can mean almost 10% of the total energy consumption.

As already mentioned, the fluid is pumped through the flow system with a pump and the flow rate is determined from at least one electrical operating parameter of the pump, such as from the electrical drive current of the pump and/or from the speed of rotation of the pump. This method of the continuous flow measurement is particularly energy-saving, since the electrical operating parameters in the electronic drive unit of the motor are quasi-automatically available and for this reason do not have to be determined separately. From an apparatus point of view, and thus in turn also with a view to the energy consumption, this solution is particularly preferable, since absolutely no additional apparatus has to be provided for the permanent monitoring of the flow rate of the fluid through the flow system.

In an embodiment which is particularly useful for practical use, the pump is driven by an electrical rotary drive, which includes a stator with a stator winding and a rotation body rotating in the fluid, with the rotation body being the rotor of the rotary drive and being magnetically supported contact-free relative to the stator. In this connection the drive and the magnetic support of the rotor form a bearingless motor.

Within the scope of this application a bearingless motor should be understood to mean a motor with a purely magnetically supported rotor, such as is described in detail in EP 1 284 415 A1 or WO 96/31934, for example, the contents of which are hereby incorporated by reference. In this connection the contact-free magnetically journalled motors of this kind are substantially characterized in that a rotation machine of this kind has a driven rotor and an electrical motor, which includes a stator and the driving rotor, with the stator also being an electromagnetic support for the driving rotor, and with the driving rotor of the electric motor with the driven rotor of the rotation machine forming a rotor unit, i.e. an integral rotor, with only one single stator being provided, which both supports and drives the integral rotor.

Any suitable sensor can be used as the calibration sensor, such as, for example, a differential pressure sensor, an impeller sensor, a sensor with a floating body, an optical sensor, and/or an acoustic sensor (such as an ultrasonic sensor). In this connection at least one pair of two corresponding ultrasonic sensors are particularly preferred for a flow system in accordance with the invention, which can work on a piezoelectric basis and can each be operated both as an ultrasonic transmitter and also as an ultrasonic receiver. The corresponding measuring system, known per se, will be described in more detail in the following description of the figures.

As has already been mentioned, the flow rate of the fluid is continually determined from the working parameters of the flow system, since the working parameter, for example the power take-up of the pump motor, is anyway often interrupted and is automatically available. It goes without saying in this connection that the flow measurement from the working parameter does not have to take place continuously, but can likewise be interrupted time-wise, whereby electrical energy in the associated evaluation electronics can be additionally saved.

In contrast, the calibration measurement with the calibration sensor takes place in pre-determined time intervals, such as periodically, i.e. at the same time intervals, for the calibration of the flow measurement.

The calibration sensor can be connected to a separate evaluation unit with an electrical power supply and thus be supplied with electrical power, and/or the evaluation unit can be switched off between two calibration measurements or put into an energy-saving state.

It will be understood that the calibration sensor can also be supplied with electrical energy with the energy supply of the control electronics of the pump motor, and/or the evaluation unit of the calibration sensor can be an integral component of the control electronics of the pump motor which can be switched off separately, for example.

The method in accordance with the invention can be used particularly advantageously in a ventricle support system for the support of human or animal blood circulation since, by means of the method in accordance with the invention, a considerable amount of electrical energy can be saved, and because the calibration of the flow rate can be carried out by non-invasive methods, for example by an ultrasonic measuring system, so that the actual measurement does not negatively influence the fluid either chemically or physically in any way at all.

In the following the process of calibration in accordance with the present invention, using a heart supporting blood pump developed by the present assignee, will be illustrated in an embodiment which is particularly relevant for practical use.

The flow measuring unit, which is a MiniDigi-Flow-Board in the present example, can be switched off for a pre-determinable period of time for the reduction of heat and of the energy consumption within a housing which houses the electrical drive. In this time interval the flow through the flow determining unit of the UltraMag device is monitored. Since the flow determining unit is not very stable for long periods of time, an offset in the flow determination is regularly corrected with measured values, which the MiniDigi-Flow-Board delivers, in order to avoid a drift in the flow determination.

In this connection the switching off of the flow measuring unit, in other words the MiniDigi-Flow-Board, can in principle take place in two ways: periodic power reduction, i.e. transition of the MiniDigi-Flow-Board into a so-called "sleep mode" and a flow determination by means of the flow determination unit of the UltraMag device, or periodic switching off of the MiniDigi-Flow-Board and a flow determination by the flow determination unit of the UltraMag device.

The embodiment in which the MiniDigi is switched off is, in many cases, to be preferred, since the switching off requires less complicated programming and is also less costly and complex, as a result of which this method is often more effective and more economical in comparison to the embodiments in which the MiniDigi is put into a sleep mode.

In one example the MiniDigi-Flow-Board is switched off for a period of 10 minutes. The flow calibrating unit of the UltraMag device is only switched on, or activated, briefly every 10 minutes, for 15 seconds for example. This allows the flow calibration unit to utilize a low pass filtered flow rate. This value is then used to determine the actual offset of the flow calculation.

When the flow calibration unit is switched off, the flow is calculated. Each time the MiniDigi-Flow-Board (or measuring unit) is switched on, the determined flow rate is calibrated.

The person averagely skilled in the art can vary the basic concept described above and adapt it to special requirements. Moreover, it goes without saying that in practice the possibility of a break-down or an interruption of the flow for example is to be taken into consideration accordingly.

In one example the flow is calculated or otherwise determined approximately every 2.6 ms. For this reason the above-described flow determination can be regarded as being quasi-continuous in relation to the frequency of the flow measurement and the calibration frequency.

The calibration method previously described can for this reason be schematically illustrated in accordance with FIG. 2a in a simplified manner.

The lower arrow in accordance with the illustration symbolizes the time axis, while the corresponding time dependencies of the operating states of the MiniDigi-Flow-Board (measuring unit) designated with C in FIG. 2a, of the UltraMag flow calibration unit designated with B in FIG. 2a and of the UltraMag flow determination unit designated with A, are shown by the bars designated with A, B and C.

In the shaded regions the associated operating state is a switched-on state, in the not-shaded regions the corresponding operating state is a switched-off state.

Coming from the left in accordance with the drawing the MiniDigi-Flow-Board (measuring unit) is initially switched off. This means that the flow is not being measured currently by means of the described ultrasonic or other sensors.

The MiniDigi (measuring unit) is then switched on between the points in time $t_1$ and $t_2$ and the actual flow rate is measured. After switching off the MiniDigi at the point in time $t_2$, the offset between the determined and measured values is calculated and thereafter used for the calibration of the flow determination.

The entire procedure is then repeated periodically, the next time being, as illustrated in FIG. 2a, again from the time period between the points in time $t_3$ and $t_4$, etc.

In the example of FIG. 2a the flow calculation takes place quasi-continuously every 2.6 ms, for which reason the bar A could be shaded completely. The calibration and the ultrasonic measurement are each only carried out every 10 minutes, as a result of which a large amount of electrical energy is saved in accordance with the invention.

Finally the associated algorithm is schematically illustrated in FIG. 2b in a simplified manner.

In this arrangement QE signifies the flow rate calculated or determined, for example, on the basis of the impeller speed and of the torque forming current. S/H is a "sample and hold element" known per se with a sample rate, e.g. in the minute range. $Q_M$ is the reference flow rate measured, for example every 10 minutes, such as by means of the described ultrasonic technology. $Q_o$ is the offset correction factor and $Q_{EC}$ the calibrated flow. LP1 designates a low pass filter with a time constant $T_1$, e.g. in the second to minute range, such as $T_1=10$ s for example, and LP2 is a low pass filter with a time constant $T_2$, e.g. in the second to minute range, such as 1 min$<T_2<$30 min.

Since the change in the hematocrit of the blood leads in principle to a change in the offset, the calibration can be accomplished by means of an offset calibration as shown schematically in FIG. 2b. The offset correction factor can additionally be filtered through a low pass filter.

The invention further relates to a flow system for the carrying out of a method in accordance with the invention.

In an embodiment, a flow system in accordance with the invention is a ventricle support system for the support of a human or animal circulation, including a pump with a bearingless motor, a control unit connected signal-wise to the bearingless motor for the control and/or regulation of one or more operating parameters of the pump, with the control unit including a determining unit for the determination of a flow rate of blood from one or more working parameter of the bearingless motor. In accordance with some embodiments, an acoustic calibration sensor is provided in this arrangement, with which the flow rate of the blood can be measured at a pre-determined point in time in a calibration measurement, and the flow rate determination can be calibrated with the help of the calibration measurement. In this arrangement the calibration measurement with the calibrating sensor can be repeated at pre-determined time intervals in the operating state. An evaluation unit is provided for the calibration sensor and can be switched off between calibration measurements, or put into an energy-saving state.

The pump and/or the control unit and/or the evaluation unit can be battery operated.

In this connection, a flow system in accordance with embodiments of the invention is designed in such a way that mechanical torque and/or motor current can be used to determine the flow rate.

Figure 3:
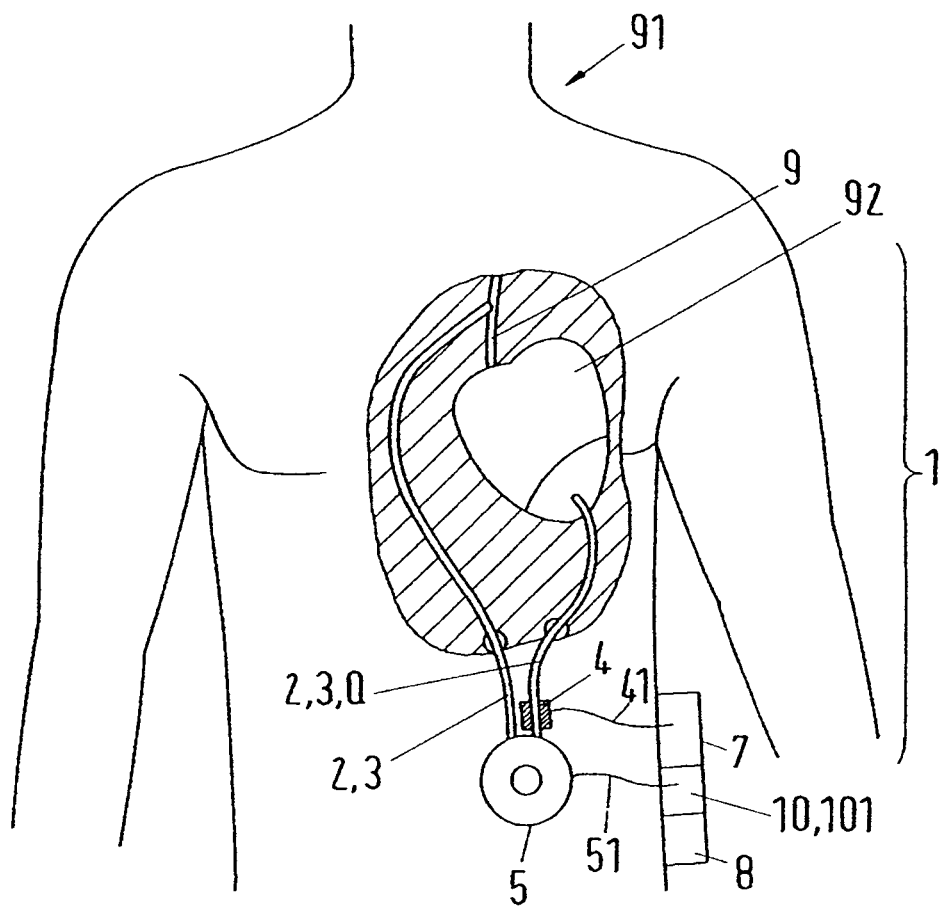
FIG. 3 schematically illustrates a ventricle support system.

FIG. 3 shows, in a schematic illustration, an embodiment of a flow system in accordance with the invention, which is designated as a whole with the reference numeral 1 in the following.

The flow system 1 of FIG. 3 is a portable ventricle support system, which can be provided both inside and outside the human body and which is connected to a circulatory system 9 of a human patient 91. The patient 91 carries all the system components of the ventricle support system 1 on or in his body, so that the patient 91 enjoys complete freedom of movement. It goes without saying that the invention is not restricted to portable systems but can also be used advantageously with stationary systems. Certain components of the flow system 1 or at least parts thereof can be battery operated, but they do not have to be.

The ventricle support system 1 includes a blood pump 5, which is driven by a bearingless motor as defined earlier, which is connected to the circulatory system 9 of the patient 91 via two flow connections 3, such as two heart cannulae 3, at a pump input and at a pump output, in a manner known per se, so that, for example for the relief of the heart 92 of the patient 91, blood 2 can be supplied via the flow connections 3 of the blood pump 5 from the circulatory system 9 and can be pumped back into the circulatory system 9 again by the pump 5 while generating a pumping power. The blood pump 5 is connected signal-wise to a control unit 10 via an electrical control and signal line 51. The control unit 10 includes a determining unit 101, with which a flow rate (Q) of the blood 2 is determined continuously from the operating parameters of the electrical drive of the blood pump 5. Moreover, the electrical drive is supplied with electrical energy and electrical control signals via the signal lead 51.

An ultrasonic calibration sensor 4 is provided at one of the two flow connections 3 which connects the blood pump 5 to the blood circulation 9 to convey blood 2. In this connection it is insignificant for the present invention whether the calibration sensor 4 is provided at the input or at the output of the blood pump 5. Depending on the type of construction of the pump, the calibration sensor 4 can be provided at the output of the blood pump 5, for example, when more space for the placing of the calibration sensor 4 is available at the output, for example. It should be understood, moreover, that the calibration sensor can be provided at any suitable point of the flow connection 3, which is not necessarily directly at or in the vicinity of the pump.

The ultrasonic calibration sensor 4 is connected signal-wise via an electrical connection 41 to an evaluation unit 7 which, on the one hand, supplies the calibration sensor 4 with electrical energy and electric signals for the production of ultrasonic impulses and, on the other hand, detects and evaluates the transit time signals measured by the calibration sensor 4. The evaluation unit 4 is in turn connected signal-wise to the control unit 10 or to the measuring unit 101, so that with the help of calibration data, which are periodically measured using the calibration sensor, for example, the determined flow rate (Q) of the blood 2, which was determined from the working parameters of the electrical drive of the blood pump 5, can be calibrated in a manner known per se, i.e. can be adjusted when necessary.

The calibration measurement using the calibration sensor 4 is preferably undertaken at periodic intervals in this arrangement, for example at an interval of up to 30 seconds, or at an interval of up to 2 minutes; in some cases it can even suffice to only undertake the calibration measurement at intervals of 10 minutes or at even longer intervals. The evaluation unit 7 of the calibration sensor 4 is switched off between calibration measurements, so that the lifetime of the energy supply 8, such as a rechargeable accumulator 8, which supplies the whole ventricle support system, is considerably increased and the accumulator 8 thus has to be recharged considerably less frequently. In addition, less heat is generated by the reduced power consumption and the lower power loss resulting therefrom.

Figure 4:
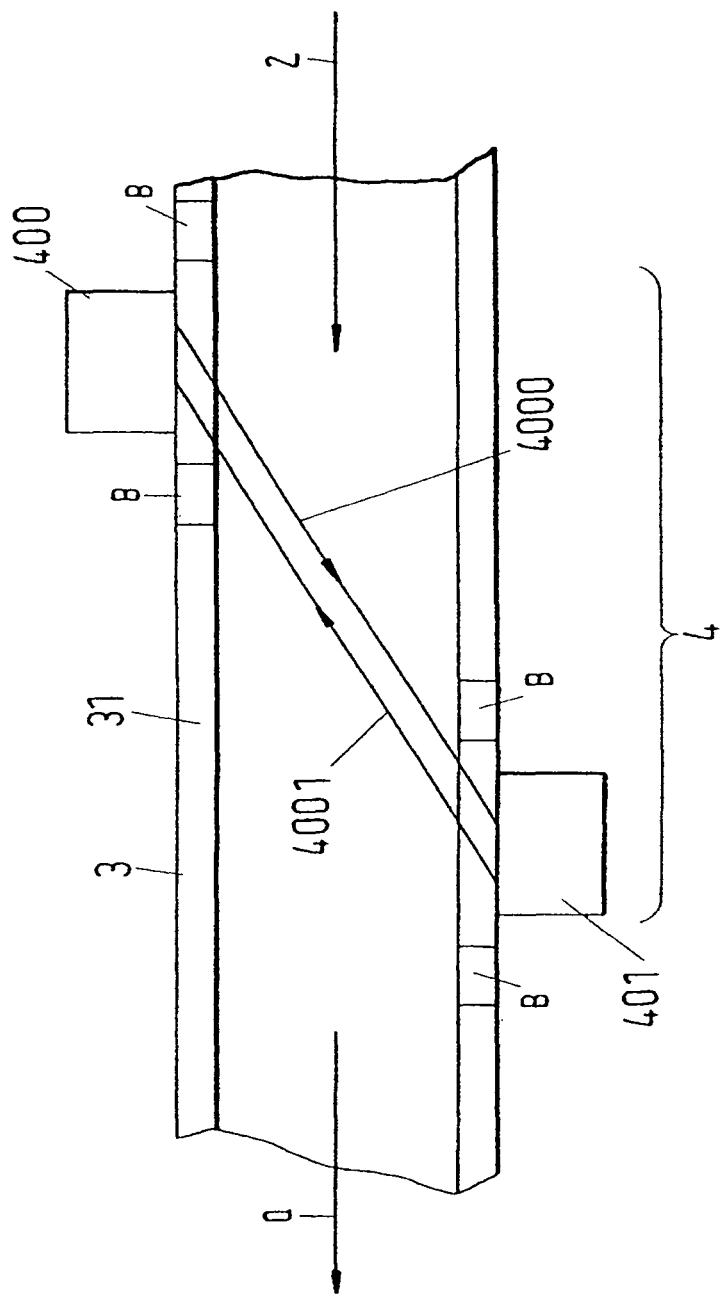
FIG. 4 shows a first embodiment of an ultrasonic calibration sensor.

In FIG. 4 a first simple embodiment of an ultrasonic calibration sensor 4 is schematically illustrated. The calibration sensor 4 includes a first piezoelectric ultrasonic sensor 400 and a second identical piezoelectric ultrasonic sensor 401, which could each work both as a transmitter and as a receiver, and are provided offset from one another in the axial direction at an external wall 31 of the flow connection 3. In the example of FIG. 4 the fluid 2, for example blood 2, flows from right to left, as indicated by the arrows, through the flow connection 3.

Now either simultaneously or in quick succession, a short first and second ultrasonic impulse or packets of ultrasonic waves 4000 and 4001 are respectively produced by the two ultrasonic sensors 400, 401. The first ultrasonic impulse 4000 is produced by the first ultrasonic sensor 400, passes through the flowing fluid 2 and is detected by the second ultrasonic sensor 401. Analogously, the second ultrasonic impulse passes from the second ultrasonic sensor 401 to the first ultrasonic sensor 400 and is detected by it.

From the detected signals, the evaluation unit 7 (not illustrated in FIG. 4) determines the transit times of the ultrasonic impulses 4000 and 4001, which are different due to the flow speed of the fluid 2, because the first ultrasonic impulse 4000 has a speed component in the flow direction of the fluid, and the second ultrasonic impulse 4001 has a speed component against the flow direction of the fluid 2. The actual flow rate (Q) of the fluid 2 can then be determined in a manner known per se from the transit time difference of the two ultrasonic impulses 4000 and 4001, and thus the flow determination which was obtained from the working parameters of the flow system can be calibrated, i.e. corrected, if necessary.

So that the measurement is not disturbed or falsified by reflections of the ultrasound in the exterior wall 31 of the flow connection 3, sound barriers B can be provided in the exterior wall 31, which refract or muffle roaming acoustic signals, so that these can basically no longer be detected by the ultrasonic sensors 400, 401.

Figure 5:
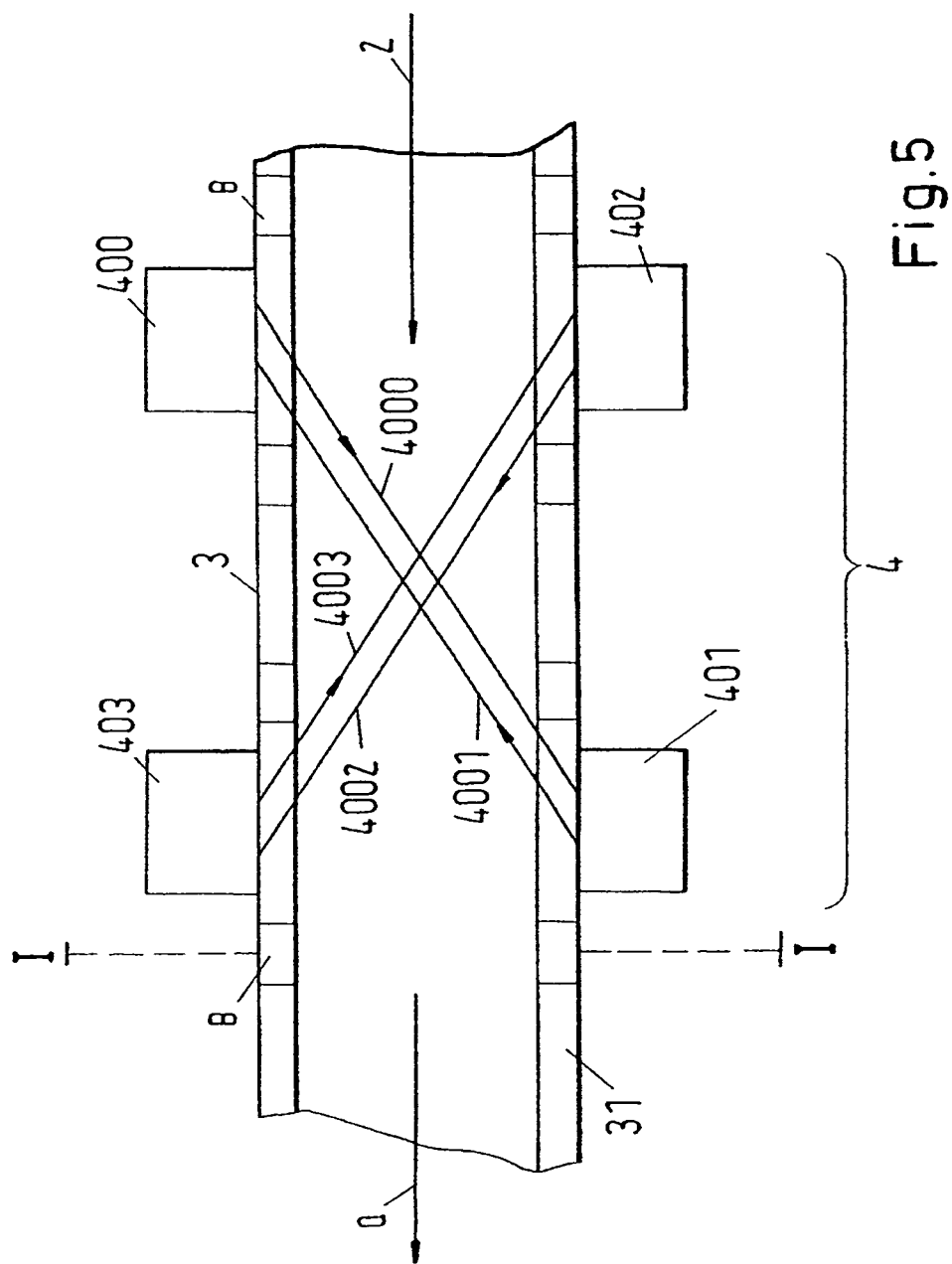
FIG. 5 shows a second embodiment of an ultrasonic calibration sensor.

A second embodiment of a calibration sensor is illustrated schematically in FIG. 5, which only differs from the example of FIG. 4 in that, in addition to the sensor pair 400 and 401, another second identical sensor pair 402 and 403 is provided, which works analogously to the sensor pair 400 and 4001 and exchanges short ultrasonic impulses 4002 and 4003 and conveys them to the evaluation unit 7 for evaluation.

The advantage of the calibration sensor 4 in accordance with FIG. 5 in comparison with the somewhat more simply constructed sensor of FIG. 4 is that a higher resolution and/or a higher precision in the calibration measurement can be achieved with the sensor of FIG. 5.

Figure 6:
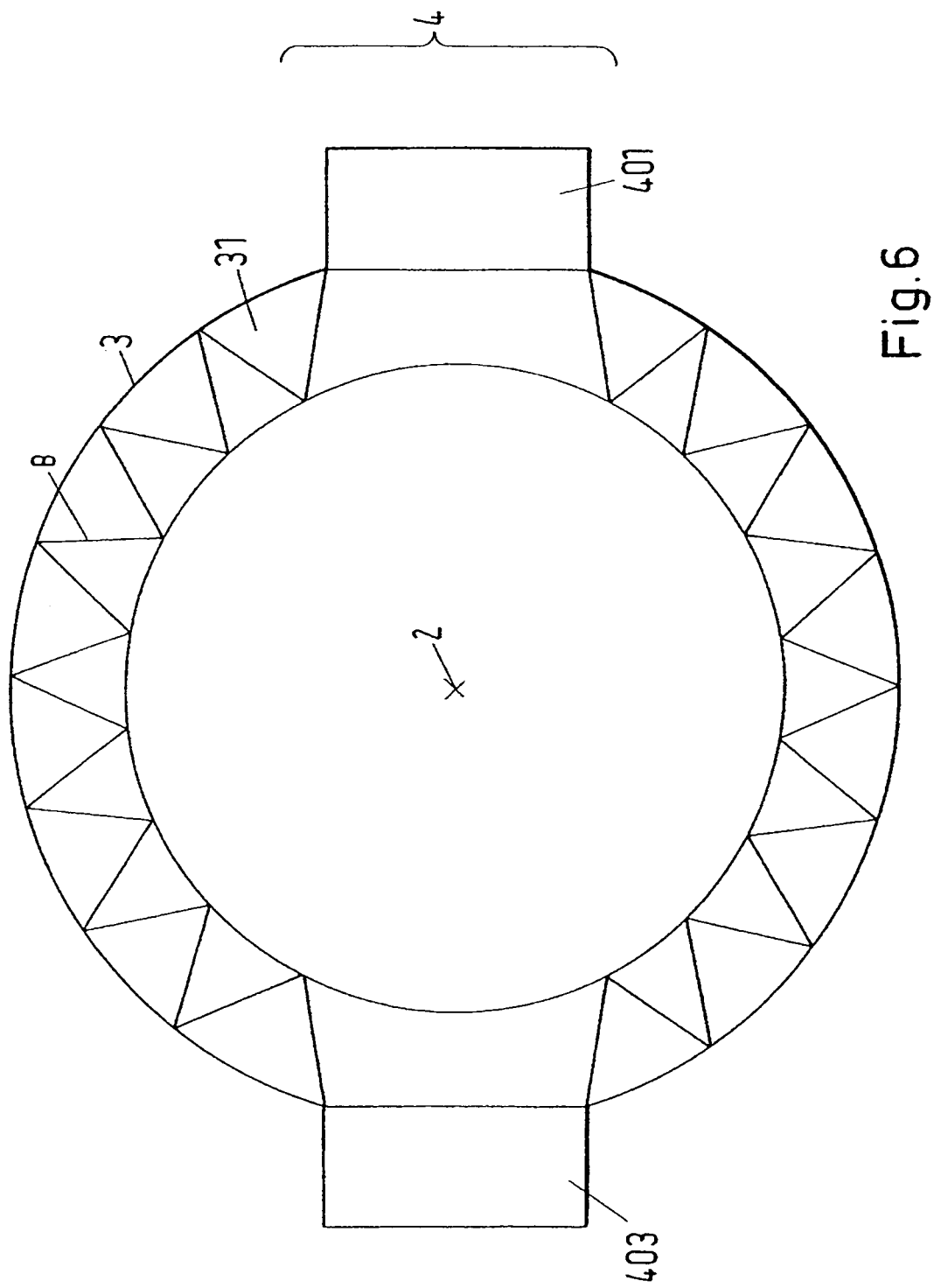
FIG. 6 is a sectional view taken along line I-I of FIG. 5.

Finally, in FIG. 6, a section along line I-I of FIG. 5 is shown, which illustrates an exemplary possible design of signal barriers B in the exterior wall 31 of the flow connection. The signal barriers B can, for example, be recesses, irregularities incorporated in the material of the exterior wall 31, or other purposefully incorporated faults, which reflect, refract and thus ultimately so strongly muffle the ultrasonic impulses circulating in the exterior wall 31 that they can no longer reach the sensors 400, 401, 402, 403, or are no longer registered by these as signals to be evaluated.

It will be understood that the embodiments discussed within the scope of this application are merely to be understood as examples, and in particular all suitable combinations and simple further developments well-known to the person averagely skilled in the art are covered by the invention.

The invention claimed is:

1. A method of calibrating a determination of a flow rate of a fluid in a flow system, wherein the flow system constitutes at least a part of a ventricle support system for the support of a human or animal blood circulation, the method comprising:
   conveying the fluid through the flow system with a pump;
   indirectly determining the flow rate based on one or more parameters of the pump;
   measuring the flow rate with a calibration sensor; and
   using the measured flow rate to calibrate the indirect determination to determine the flow rate.

2. The method of claim 1, wherein the measuring takes place at discrete time intervals.

3. The method of claim 2, wherein the measuring is periodic.

4. The method of claim 2, wherein the measuring further comprises using an evaluation unit in communication with the calibration sensor, the method further comprising powering off the evaluation unit or putting the evaluation unit in a sleep mode when the measuring is not occurring.

5. The method of claim 1, wherein the parameters comprise at least one member of the group consisting of: torque of the pump, electrical drive current of the pump, power of the pump, angular velocity of the pump, angular frequency of the pump, and induced voltage of drive phases of the pump.

6. The method of claim 1, wherein the parameters comprise at least one member of a first group consisting of torque of the pump and electrical drive current of the pump, and at least one member of a second group consisting of angular speed of the pump, angular frequency of the pump, and induced voltage of drive phases of the pump.

7. The method of claim 1, wherein the determining is continuous.

8. A calibration system for calibrating a determination of a flow rate of a fluid in a flow system, wherein the fluid is conveyed through the flow system with a pump, the calibration system comprising:
   a determining unit for indirectly determining the flow rate based on one or more parameters of the pump; and
   a calibration sensor for measuring the flow rate;
   wherein the calibration system is configured for the measured flow rate to calibrate the indirect determination of the determining unit to determine the flow rate;
   wherein the flow system constitutes at least a part of a ventricle support system for the support of a human or animal blood circulation.

9. The calibration system of claim 8, further configured for the calibration sensor to measure the flow rate at discrete time intervals.

10. The calibration system of claim 8, further comprising an evaluation unit for measuring the flow rate in collaboration with the calibration sensor, the system further being configured to power off the evaluation unit or put the evaluation unit in a sleep mode when the sensor and the evaluation unit are not measuring the flow rate.

11. The calibration system of claim 8, wherein the parameters comprise at least one member of the group consisting of: torque of the pump, electrical drive current of the pump, power of the pump, angular velocity of the pump, angular frequency of the pump, and induced voltage of drive phases of the pump.

12. The calibration system of claim 8 wherein the parameters comprise at least one member of a first group consisting of torque of the pump and electrical drive current of the pump, and at least one member of a second group consisting of angular speed of the pump, angular frequency of the pump, and induced voltage of drive phases of the pump.

13. The calibration system of claim 8, wherein the calibration sensor comprises a member of the group consisting of a differential pressure sensor, an impeller sensor, a sensor with a floating body, an acoustic sensor, and an ultrasonic sensor.

14. The calibration system of claim 8, wherein the determining is continuous.

15. A calibration system for calibrating a determination of a flow rate of a fluid in a flow system, wherein the fluid is conveyed through the flow system with a pump, the calibration system comprising:
 a determining unit for indirectly determining the flow rate based on one or more parameters of the pump; and
 a calibration sensor for measuring the flow rate;
 wherein the calibration system is configured for the measured flow rate to calibrate the indirect determination of the determining unit to determine the flow rate;
 wherein the pump comprises a bearingless motor.

16. A flow system configured for a fluid to flow therein, comprising:
 at least one fluid conduit;
 a pump for pumping the fluid through the fluid conduit;
 a determining unit for indirectly determining a flow rate of the fluid within the fluid conduit based on one or more parameters of the pump; and
 a calibration sensor for measuring the flow rate;
 wherein the system is configured for the measured flow rate to calibrate the indirect determination of the determining unit to determine the flow rate;
 wherein the flow system constitutes at least a part of a ventricle support system for the support of a human or animal blood circulation.

17. The system of claim 16, wherein the parameters comprise at least one member of the group consisting of: torque of the pump, electrical drive current of the pump, power of the pump, angular velocity of the pump, angular frequency of the pump, and induced voltage of drive phases of the pump.

18. The system of claim 16, wherein the parameters comprise at least one member of a first group consisting of torque of the pump and electrical drive current of the pump, and at least one member of a second group consisting of angular speed of the pump, angular frequency of the pump, and induced voltage of drive phases of the pump.

* * * * *